United States Patent [19]

Solyom et al.

[11] 4,218,446

[45] Aug. 19, 1980

[54] SUBSTITUTED STEROID-SPIRO-OXAZOLIDINONE DERIVATIVES AND A PROCESS FOR THE PREPARATION THEREOF

[75] Inventors: Sándor Sólyom; Lajos Toldy; Katalin Szilágyi née Faragó; Inge Schäfer; Eleonóra Szondy; János Borvendég; Ilona Hermann née Szente, all of Budapest, Hungary

[73] Assignee: Richter Gedeon Vegyészeti Gyár Rt, Budapest, Hungary

[21] Appl. No.: 25,080

[22] Filed: Mar. 29, 1979

[30] Foreign Application Priority Data

Jan. 4, 1978 [HU] Hungary .............................. GO 1397

[51] Int. Cl.$^2$ ............................................. A61K 31/58
[52] U.S. Cl. ................................. 424/241; 260/239.5
[58] Field of Search ....................... 260/239.5; 424/241; /Steroids MS File

[56] References Cited

U.S. PATENT DOCUMENTS 4,085,522  11/1977  Kekesy et al. .................. 260/239.57

Primary Examiner—Elbert L. Roberts
Attorney, Agent, or Firm—Karl F. Ross

[57] ABSTRACT

Diuretic pharmaceutically active steroid-spiro-oxazolidinone compounds of the formula (I),

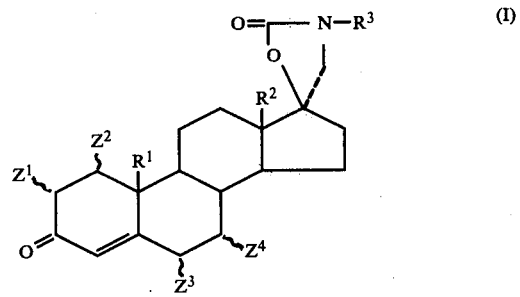

wherein
- $R^1$ is hydrogen or methyl,
- $R^2$ is $C_{1-4}$ alkyl,
- $R^3$ is hydrogen, $C_{1-4}$ alkyl or $C_{2-4}$ alkenyl,
- $Z^1$ and $Z^2$ each are hydrogen or together form a second valence bond, or $Z^1$ is hydrogen and $Z^2$ is $R^4$—S—,
- $Z^3$ and $Z^4$ each are hydrogen or together form a second valence bond, or $Z^3$ is hydrogen and $Z^4$ is $R^4$—S—, with at least one of the pairs $Z^1$-$Z^2$ and $Z^3$-$Z^4$ representing hydrogen and an $R^4$—S— group, and
- $R^4$ is hydrogen or alkyl, alkenyl, aralkyl or acyl with up to 7 carbon atoms, provided that when $Z^1$ and $Z^2$ together form a valence bond, or $Z^1$ represents a hydrogen atom and $Z^2$ and $R^4$—S— group then $R^1$ is methyl.

6 Claims, No Drawings

SUBSTITUTED STEROID-SPIRO-OXAZOLIDINONE DERIVATIVES AND A PROCESS FOR THE PREPARATION THEREOF

This invention relates to steroid-spiro-oxazolidinone derivatives if the formula (I)

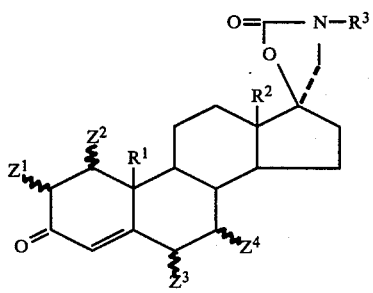

wherein
- $R^1$ is hydrogen or methyl,
- $R^2$ is $C_{1-4}$ alkyl,
- $R^3$ is hydrogen, $C_{1-4}$ alkyl or $C_{2-4}$ alkenyl,
- $Z^1$ and $Z^2$ each are hydrogen or together form a second valence bond, or $Z^1$ is hydrogen and $Z^2$ is an $R^4$—S— group,
- $Z^3$ and $Z^4$ each are for a hydrogen or together form a second valence bond, or $Z^3$ is hydrogen and $Z^4$ is $R^4$—S— with at least one of the pairs $Z^1$-$Z^2$ and $Z^3$-$Z^4$ representing hydrogen and $R^4$—S—, and
- $R^4$ is a hydrogen or alkyl, alkenyl, aralkyl or acyl with up to 7 carbon atoms, provided that when $Z^1$ and $Z^2$ together form a valence bond, or $Z^1$ is hydrogen and $Z^2$ is $R^4$—S— then $R^1$ is methyl group; the invention also relates to pharmaceutical compositions containing these compounds to a process for the preparation of these compounds and a method of treatment using them.

The compounds of formula (I) include all the stereoisomers and isomeric mixtures thereof.

The compounds of the formula (I) are new and possess valuable pharmacological activity. They can also exert outstanding antialdosterone effects.

It is known that aldosterone, a hormone of the adrenal cortex, causes sodium retention and stimulates the excretion of potassium. In certain pathological states of the adrenal gland, hyperaldosteronism takes place, which is responsible for the occurence of oedmeas of hepatic, renal and cardiac origin. In such instances aldosterone always has a high concentration in the blood.

Compounds with aldosterone-antagonizing effects are capable of inhibiting the harmful effects of the hormone exerted in these pathological states. These compounds enhance the excretion of sodium ions through the tubular cells of the kidney, evacuating thereby the oedemas. Thus the aldosterone-antagonizing agents exert diuretic effects, and represent a particularly important group of diuretics. The compound of the formula (I) belong to this valuable group of biologically active agents.

The new steroid derivatives of the formula (I) are prepared according to the invention by reacting a compound of the formula (II),

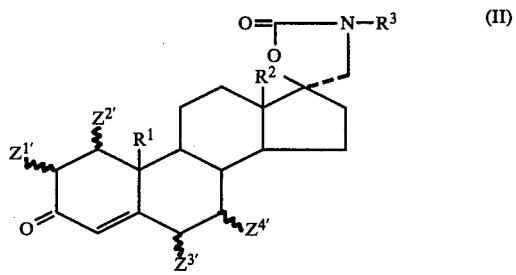

wherein
- $Z^{1'}$ and $Z^{2'}$ each are hydrogen or together form a valence bond,
- $Z^{3'}$ and $Z^{4'}$ each are hydrogen or together form a valence bond, with at least one of the pairs $Z^{1'}$-$Z^{3'}$ and $Z^{2'}$-$Z^{4'}$ standing for a valence bond, with a thiol of the formula (III)

$$R^4\text{—SH.} \qquad (III)$$

The reaction can be performed in the presence or absence of a solvent, optionally in the presence of a catalyst.

According to a preferred method of the invention a $\Delta^{4,6}$-, $\Delta^{1,4}$- or $\Delta^{1,4,6}$-unsaturated steroid-spiro-oxazolidinone of the formula (II) is heated gently in a $C_{1-4}$-thiolalkanecarboxylic acid, such as thioacetic acid or thiopropionic acid, and the resulting addition product is separated. This method can be for the preparation of $7\alpha$-, $1\alpha$- or 1,7-bis(alkanoylthio)-androst-4-ene-3-one-spiro-oxazolidinone derivatives.

When a 19-nor-steroid-spiro-oxazolidinone with $\Delta^{4,6}$-3-one structure is used as the starting substance in the above process, the respective $7\alpha$-alkanoylthio compounds of the formula (I) are obtained.

When the compounds of the ormula (II) are reacted with an alkyl mercaptan, generally a prolonged heating is required in order to complete the reaction. In such instances the reaction is performed preferably in the presence of a basic catalyst, such as piperidine or a quaternary ammonium-type ion exchange resin in the hydroxy cycle. In this way $7\alpha$-alkylthio-steroid-17-spiro-oxazolidinone derivatives can be prepared.

The compounds of the formula (II), used as starting substances in the process of the invention, can be prepared as described in the Belgian patent specification No. 864,689.

The aldosterone-antagonizing effects of the new compounds according to the invention were investigated according to the method of C. M. Kagawa (C. M. Kagawa et al.: J. Pharmacol. Exp. Ther. 126, 123 (1959).

The adrenal glands of rats were removed 18 hours before the treatment. The compound under examination was administered to the animals together with a subcutaneous dosage of 12.5 μg. of deoxycorticosterone acetate (DOCA), a substance capable of supplementing the aldosterone effect, and the sodium and potassium content of the urine was determined by flame photometry. In the comparative test an oral dosage of 480 μg. of spironolactone [17α-carboxyethyl-17β-hydroxy-7α-acetylthio-androst-4-en-3-one-lactone]was administered. The results were evaluated by calculating the log (10Na+/K+) values. The results are summarized in Table 1.

Table 1

| Compound | Dosage μg/animal p.o. | No. of animals | log(10 Na+/K+) | DOCA blocking effect, % | Index of activity T/Sp |
|---|---|---|---|---|---|
| DOCA | — | 8 | 0.73 | — | — |
| Spironolactone | 480 | 8 | 1.52 | 108 | |
| 7α-Acetylthio-estr-4-en-3-one-17S-spiro-5'-(2'-oxo-3'-methyl-oxazolidine) | 480 | 8 | 1.43 | 96 | 0.94 |
| DOCA | — | 8 | 0.60 | — | — |
| Spironolactone | 480 | 8 | 1.05 | 75 | |
| 7α-Ethylthio-androst-4-en-3-one-17S-spiro-5'-(2'-oxo-3'-methyl-oxazolidine) | 480 | 8 | 1.09 | 82 | 1.04 |

T/Sp = test substance/spironolactone

From the above Table it will be seen that 7α-acetylthio-estr-4-en-3-one-17S-spiro-5'-(2'-oxo-3'-methyl-oxazolidine) and 7α-ethylthio-androst-4-en-3-one-17S-spiro-5 '-(2'-oxo-3'-methyl-oxazolidine) significantly inhibit the mineralocorticoid effect of DOCA on rats. The inhibiting effect of the latter compound, measured on rats, is higher than that of spironolactone. At the same time, the compound according to the invention does not have any undesired endocrine side-effect, such as antiestrogenic, androgenic or antiandrogenic effect.

The results of the endocrinological examination of 7α-ethylthio-androst-4-en-3-one-17S-spiro-5'-(2'-oxo-3'-methyl-oxazolidine) are described below.

The uterotropic and antiestrogenic effects of the compound were examined on infantile female mice according to the method of Edgren (R. Dorfman: Methods in Hormone Research, Acad. Press, 1962). No uterotropic effect could be observed when administering the compound in daily subcutaneous dosages of 30mg./kg. The examination of the antiestrogenic effect showed that the compound did not significantly decrease the uterotropic effect of estradiol benzoate, introduced simultaneously for 3 days in daily dosages of 0.1 μg./animal.

The androgenic and antiandrogenic effects of the compound were examined on castrated male rats according to the method of Dorfman (R. Dorfman: Methods in Hormone Research, Acad. Press, 1962). No androgenic effect could be observed when administering the compound for 7 days in daily subcutanous dosages of 1 mg./animal. In this test the compound did not inhibit the androgenic effect of testosterone propionate administered in daily dosages of 50 μg.

When spironolactone was administered into the animals in daily subcutaneous dosages of 1 mg., a significant decrease in the androgenic effect of testosterone propionate, introduced simultaneously with spironolactone, could be observed. The androgenic effect was evaluated by measuring the weight increase of the accessory sexual glands (seminal vesicle, ventral prostatic lobe) of the animals. The weights of these glands were smaller by 49.2% and 42.5%, respectively, in comparison to those of the glands removed from animals receiving testosterone propionate alone.

The compounds of the formula (I) can be converted into pharmaceutical compositions for enteral or parenteral administration. These pharmaceutical compositions may be solid or liquid preparations, such as tablets, coated tablets, capsules, pills, suppositories, emulsions, suspensions, injectable solutions, etc., and can be prepared by conventional methods, utilizing pharmaceutically acceptable inert carriers, such as talc, lactose, magnesium stearate, starch, water, vegetable oils, waxes, etc. and/or other additives, such as preservatives, stabilizers, flavoring agents, surfactants, salts for adjusting the osmotic pressure, etc.

The invention is elucidated in detail by the aid of the following non-limiting Examples.

EXAMPLE 1

7α-Acetylthio-androst-4-en-3-one-17S-spiro-5'-(2'-oxo-3'-methyl-oxazolidine)

A mixture of 3.50 g. of androst-4,6-dien-3-one-17S-spiro-5'-(2'-oxo-3'-methyl-oxazolidine) and 3.5 ml. of thioacetic acid is heated on a steam bath for 1.5 hours. The excess of thioacetic acid is evaporated in vacuo, the residue is triturated with isopropyl ether, and the separated substance is filtered off. The resulting 4.03 g. of crude product are dissolved in 120 ml. of warm ethyl acetate, the solution is decolored with charcoal, filtered, and evaporated to a final volume of about 35 ml. 2.20 g. 7α-acetylthio-androst-4-en-3-one-17S-spiro-5'-(2'-oxo-3'-methyl-oxazolidine) separate from the concentrate; m.p.: 218°–219° C., $[\alpha]_D^{20} = -48°$ (c=0.5, in chloroform), UV $\lambda_{max.}^{EtOH} = 237$ μm (E=16,500).

EXAMPLE 2

1α-Acetylthio-androst-4-en-3-one-17S-spiro-5'-(2'-oxo-3'-methyl-oxazolidine)

One proceeds as described in Example 1 with the difference that 4.0 g. of androst-1,4-dien-3-one-17S-spiro-5'-(2'-oxo-3'-methyl-oxazolidine) are used as starting substance. 3.55 g. of crude 1α-acetylthio-androst-4-en-3-one-17S-spiro-5'-(2'-oxo-3'-methyl-oxa-zolidine) are obtained; m.p.: 204°–205° C. This crude product is dissolved in 35 ml. of ethyl acetate, and the solution is evaporated to one-fourth of its original volume. 2.37 g. of the purified product are obtained; m.p.: 204°–206° C., $[\alpha]_D^{20} = +43.8°$ (c=1, in chloroform), UV $\lambda_{max.}^{EtOH} = 240$ μm (E=16,300).

EXAMPLE 3

1ξ, 7ξ-bis(Acetylthio)-androst-4-en-3-one-17S-spiro-5'-(2'-oxo-3'-methyl-oxazolidine)

A mixture of 1.20 g. of androst-1,4,6-trien-3-one-17S-spiro-5'(2'-oxo-3'-methyl-oxazolidine) and 2 ml. of thioacetic acid is heated on a steam bath for 1.5 hours. The excess of thioacetic acid is evaporated is vacuo, the oily residue is triturated with isopropyl ether, then the separated crystalline substance is filtered off and washed with cold isopropyl either. The resulting crude product, weighing 1.64 g., is dissolved in 10 ml. of acetone at room temperature, the solution is decolourized with charcoal, filtered, evaporated to the half of its original volume at room temperature under reduced pressure, and 14 ml. of isopropyl ether are added to the concentrate. The separated product is filtered off, 1.10 g. of pure 1 ξ, 7ξ-bis(acetylthio)-androst-4-en-3-one-17S-spiro-5'-(2'-oxo-3'-methyl-oxazolidine) are obtained. The spectroscopic data of the product are as follows:

UV $\lambda_{max}.^{EtOH}=237$ μm (E=17,000).

IR $\nu_{max}.=1615$ (C═C), 1760 and 1690 (C═O) cm$^{-1}$.

NMR (CDCl$_3$):δ=2.85 (3H, s, —NCH$_3$), 2.40 (6H, s, acetylthio), 5.75 (1H, broad, Δν=4 Hz, ═CH) ppm.

EXAMPLE 4

7α-Acetylthio-estr-4-en-3-one-17S-spiro-5'-(2'-oxo-3'-methyl-oxazolidine)

A mixture of 0.96 g. of estr-4,6-dien-3-one-17S-spiro-5'-(2'-oxo-3'-methyl-oxazolidine) and 1 ml. of thioacetic acid is heated on a steam bath for 1 hour. The excess of thioacetic acid is distilled off at 50° C. under reduced pressure, and the residue is recrystallized twice from acetone. 0.17 g. of 7α-acetylthio-estr-4-en-3-one-17S-spiro-5'-(2'-oxo-3'-methyl-oxazolidine) are obtained; m.p.: 203°–206° C., $[\alpha]_D^{20}=-89.7°$ (c=0.5, in chloroform), UV $\lambda_{max}.^{EtOH}=236$ μm (E=20,600).

EXAMPLE 5

7α-Acetylthio-13β-ethyl-gon-4-en-3-one-17S-spiro-5'-(2'-oxo-3'-methyl-oxazolidine)

A mixture of 1.4 g. of 13β-ethyl-gona-4,6-dien-3-one-17S-spiro-5'-(2'-oxo-3'-methyl-oxazolidine) and 1.4 ml. of thioacetic acid is heated on a steam bath for 1 hour. The excess of thioacetic acid is distilled off in vacuo at 50° C., and the oily residue is triturated with a 1:1 mixture of ethyl acetate and isopropyl ether. The resulting solid is recrystallized from a 1:1 mixture of methanol and isopropyl ether. 0.71 g. of 7α-acetylthio-13β-ethyl-gon-4-en-3-one-17S-spiro-5'-(2'-oxo-3'-methyl-oxazolidine) are obtained; m.p.: 135°–138° C., $[\alpha]_D^{20}=-73.1°$ (c=0.5, in chloroform), UV $\lambda_{max}.^{EtOH}=236$ μm (E=18,800).

EXAMPLE 6

7α-Ethylthio-androst-4-en-3-one-17S-spiro-5'-(2'-oxo-3'-methyl-oxazolidine)

A mixture of 2.1 g. of androst-4,6-dien-3-one-17S-spiro-5'-(2'-oxo-3'-methyl-oxazolidine), 1.3 ml. of piperidine and 12 ml. of ethyl mercaptan is refluxed for 48 hours. Within this period a yellow solid separates from the mixture. At the end of the reaction the separated substance is dissolved by adding 50 ml. of benzene to the mixture, and the resulting solution is evaporated in vacuo. The residue is crystallized by triturating it with cold ethyl acetate. The separated crystalline crude product, weighing 1.02 g., is filtered off and recrystallized from 35 ml. of ethyl acetate. 0.55 g. of 7α-ethylthio-androst-4-en-3-one-17S-spiro-5'-(2'-oxo-3'-methyl-oxazolidine) are obtained; m.p.: 265°–266° C., $[\alpha]_D^{20}=-30.8°$ (c=1, in chloroform), UV $\lambda_{max}.^{EtOH}=238$ μm (E=14,600).

EXAMPLE 7

7α-Ethylthio-estr-4-en-3-one-17S-spiro-5'-(2'-oxo-3'-methyl-oxazolidine)

A mixture of 2.17 g. of estr-4,6-dien-3-one-17S-spiro-5'-(2'-oxo-3'-methyl-oxazolidine), 1.3 ml. of piperidine and 12 ml. of ethyl mercaptan is stirred and refluxed for 4 hours. Thereafter the reaction mixture is cooled and the separated crude product is filtered off. The crude product, weighing 1.87 g., is recrystallized from 35 ml. of ethanol to yield 1.62 g. of pure 7α-ethylthio-estr-4-en-3-one-17S-spiro-5'-(2'-oxo-3'-methyl-oxazolidine); m.p.: 216°–218° C., $[\alpha]_D^{20}=-57.7°$ (c=0.5, in chloroform), UV $\lambda_{max}.^{EtOH}=237$ μm (E=18,000).

EXAMPLE 8

Preparation of a Pharmaceutical Composition

Coated tablets for oral administration, containing 25 mg. of active agent, are prepared from the following components:

| | |
|---|---|
| 7α-ethylthio-androst-4-en-3-one-17S-spiro-5'-(2'-oxo-3'-methyl-oxazolidine) | 25 mg. |
| maize starch | 128 mg. |
| polyethylene glycol 6000 | 40 mg. |
| talc | 6 mg. |
| magnesium stearate | 1 mg. |
| average weight: | 200 mg. |

The tablets are provided with a film coating or sugar coating.

What we claim is:

1. 7α-Acetylthio-estr-4-en-3-one-17S-spiro-5'-(2'-oxo-3'-methyl-oxazolidine).

2. 7α-Ethylthio-androst-4-en-3-one-17S-spiro-5'-(2'-oxo-3'-methyl-oxazolidine).

3. A steroid-spiro-oxazolidinone compound of the formula (I)a

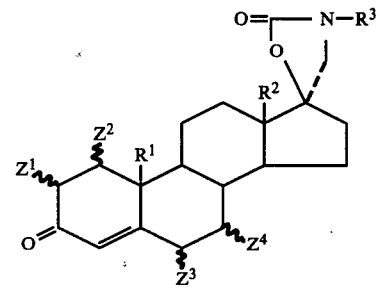

wherein
 R$^1$ is hydrogen or methyl,
 R$^2$ is C$_{1-4}$ alkyl,
 R$^3$ is hydrogen, C$_{1-4}$ alkyl or C$_{2-4}$ alkenyl,
 Z$^1$ and Z$^2$ each are hydrogen or together form a second valence bond, or Z$^1$ is hydrogen and Z$^2$ is R$^4$—S—,
 Z$^3$ and Z$^4$ each are hydrogen or together form a second valence bond, or Z$^3$ is hydrogen and Z$^4$ is R$^4$—S—, with at least one of the pairs Z$^1$-Z$^2$ and Z$^3$-Z$^4$ representing hydrogen and R$^4$—S—, and
 R$^4$ is hydrogen or alkyl, alkenyl, or alkanoyl of up to 7 carbon atoms, provided that when Z$^1$ and Z$^2$ together form a valence bond, or Z$^1$ is hydrogen and Z$^2$ is R$^4$—S—,; R$^1$ is methyl, or a stereoisomer thereof.

4. A pharmaceutical composition containing a compound as defined in claim 3, together with a pharmaceutically acceptable carrier.

5. A method of treating a diuretic condition in an animal subject which comprises the step of administering an effective amount of a compound as defined in claim 3 or a stereoisomer thereof.

6. A method of making a compound as defined in claim 3 which comprises reacting a compound of the formula (II)
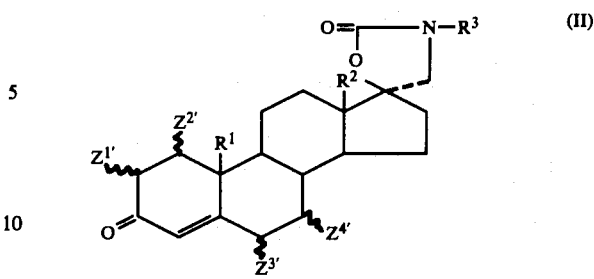
wherein $Z^{1'}$ and $Z^{2'}$ are each hydrogen or together form a valence bond, $Z^{3'}$ and $Z^{4'}$ are each hydrogen or together form a valence bond, with $Z^{1'}$-$Z^{2'}$ or $Z^{3'}$-$Z^{4'}$ forming at least one valence bond, with a thiol of the formula
$R^4$—SH.
* * * * *